(12) United States Patent
Hsu et al.

(10) Patent No.: US 8,111,817 B2
(45) Date of Patent: Feb. 7, 2012

(54) PORTABLE TELE-HOMECARE MONITORING SYSTEM AND METHOD FOR THE SAME

(75) Inventors: Yeh-Liang Hsu, Jhongli (TW);
Chang-Huei Wu, Jhongli (TW);
Chih-Ming Cheng, Jhongli (TW);
Hung-Hsiang Ma, Jhongli (TW)

(73) Assignee: Yuan Ze University, Taoyuan County (TW)

( * ) Notice: Subject to any disclaimer, the term of this patent is extended or adjusted under 35 U.S.C. 154(b) by 1466 days.

(21) Appl. No.: 11/594,803

(22) Filed: Nov. 9, 2006

(65) Prior Publication Data

US 2007/0264931 A1    Nov. 15, 2007

(30) Foreign Application Priority Data

Mar. 28, 2006   (TW) ................................ 95110799 A

(51) Int. Cl.
*H04M 11/00*    (2006.01)
(52) U.S. Cl. ................. 379/106.02; 379/106.01; 379/37; 379/90.01
(58) Field of Classification Search ............. 379/106.02, 379/106.01, 37–51, 90.01, 93.05; 340/538.11, 340/539.12, 531; 600/300, 301; 702/19
See application file for complete search history.

(56) References Cited

U.S. PATENT DOCUMENTS

| 2001/0044588 | A1* | 11/2001 | Mault | 600/549 |
| 2006/0154642 | A1* | 7/2006 | Scannell | 455/404.1 |
| 2006/0202816 | A1* | 9/2006 | Crump et al. | 340/539.12 |

FOREIGN PATENT DOCUMENTS

| TW | 400503 | 1/2000 |
| TW | M280207 | 11/2005 |

* cited by examiner

*Primary Examiner* — Melur Ramakrishnaiah
(74) *Attorney, Agent, or Firm* — Rosenberg, Klein & Lee

(57) ABSTRACT

A portable tele-homecare monitoring system and method for the same overcomes the problem of medical monitoring requiring a large organized system, with the associated high costs and disadvantages generated due to the large amount of equipment required by the prior art. The present invention allows a user to access home monitoring data by a portable electronic device, an application program or explorer via the Internet from a distributed data server. The portable tele-homecare monitoring system does not require a server and is designed to be modular and portable, so it costs are reduced and so that the design is flexible.

20 Claims, 4 Drawing Sheets

PORTABLE TELE-HOMECARE MONITORING SYSTEM AND METHOD FOR THE SAME

BACKGROUND OF THE INVENTION

1. Field of the Invention

This invention relates to a tele-homecare monitoring system and a method thereof and, more particularly, to a portable tele-homecare monitoring system and method of the same that provides environmental and health monitoring within a domestic residence.

2. Description of the Prior Art

Many tele-homecare monitoring systems are combined with information and communication technology for providing personal health management and services. Tele-homecare systems are widely used throughout Europe, North American, and Japan. Tele-homecare systems provide long-time monitoring of vital physiology signals and transmit them to a centralized database for storage and management via the Internet for use by a hospital or a similar healthcare provider.

TW patent no. 400503 proposed an "A packet-based tele-medicine system for communicating information between central monitoring stations and remote patient monitoring stations." This patent provides a packet-based tele-medicine system for transmitting video, voice and medical data between a central monitoring station and a patient's monitoring station which is remotely-located with respect to the central monitoring station. The packet-based tele-medicine system diagram of this patent is shown in FIG. 1. The packet-based tele-medicine 10 consists of a pair of central monitoring stations 11, communicating via a wired or wireless method via the Internet 16 and a pair of patient monitoring stations 18 communicating with the central monitoring station 11. The central monitoring station 11 can be located in either a home of doctor 12, a doctor's clinic 13, or a hospital 14 and communicates via the wired or wireless method via the Internet 16.

TW patent no. M280207 proposed a "remote home care system." The system diagram of this patent is shown in FIG. 2. The system includes a plurality of individual portable medical devices 20 for measuring vital physiology signals and recoding the subsequent data. A data transmitter unit 22 receives the vital physiology signals and records data for transmission via the Internet. A central monitor station 24 receives the outputted vital physiology signals and data from the data transmitter unit 22 via the Internet.

The system architecture as described above is very large. The system kernel is based in a hospital and the ISP so that the equipment is expensive and inflexible.

SUMMARY OF THE INVENTION

To solve the above problems, it is an object of the present invention to provide a portable tele-homecare monitoring system and method for the same. The method provides health data and an environmental data of each home and transmits, stores and analyzes the data. Thereby, anyone can use the portable electrical device to search for the heath data and the environmental data for anyone via the Internet.

The present invention proposes a portable tele-homecare monitoring system, comprising: a distributed data server; a centralized database coupled to the distributed data server for storing a plurality of health data and environmental data for a plurality of users; an application server coupled to the distributed data server and the centralized database, the application server includes an application program; a plurality of home sensors coupled to the distributed data server for detecting the health data and the environmental data of the users; and a portable electronic device embedded in a browser for coupling with the application server and for accessing the health data and the home environment data of the users via the application program.

The present invention proposes a method of portable tele-homecare monitor, comprising: transmitting a plurality of home monitoring data detected via a plurality of home sensors to a distributed data server; storing the home monitoring data from the home sensors processed and calculated from the distributed data server; using a search program for transmitting a search requirement command to the distributed data server; and transmitting the home monitoring data to a portable electronic device and then to the distributed data server.

The present invention is designed to be modular and portable so that costs are decreased and there is increased design flexibility due to the omission of the special server.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DETAILED DESCRIPTION OF THE INVENTION

Figure 1:
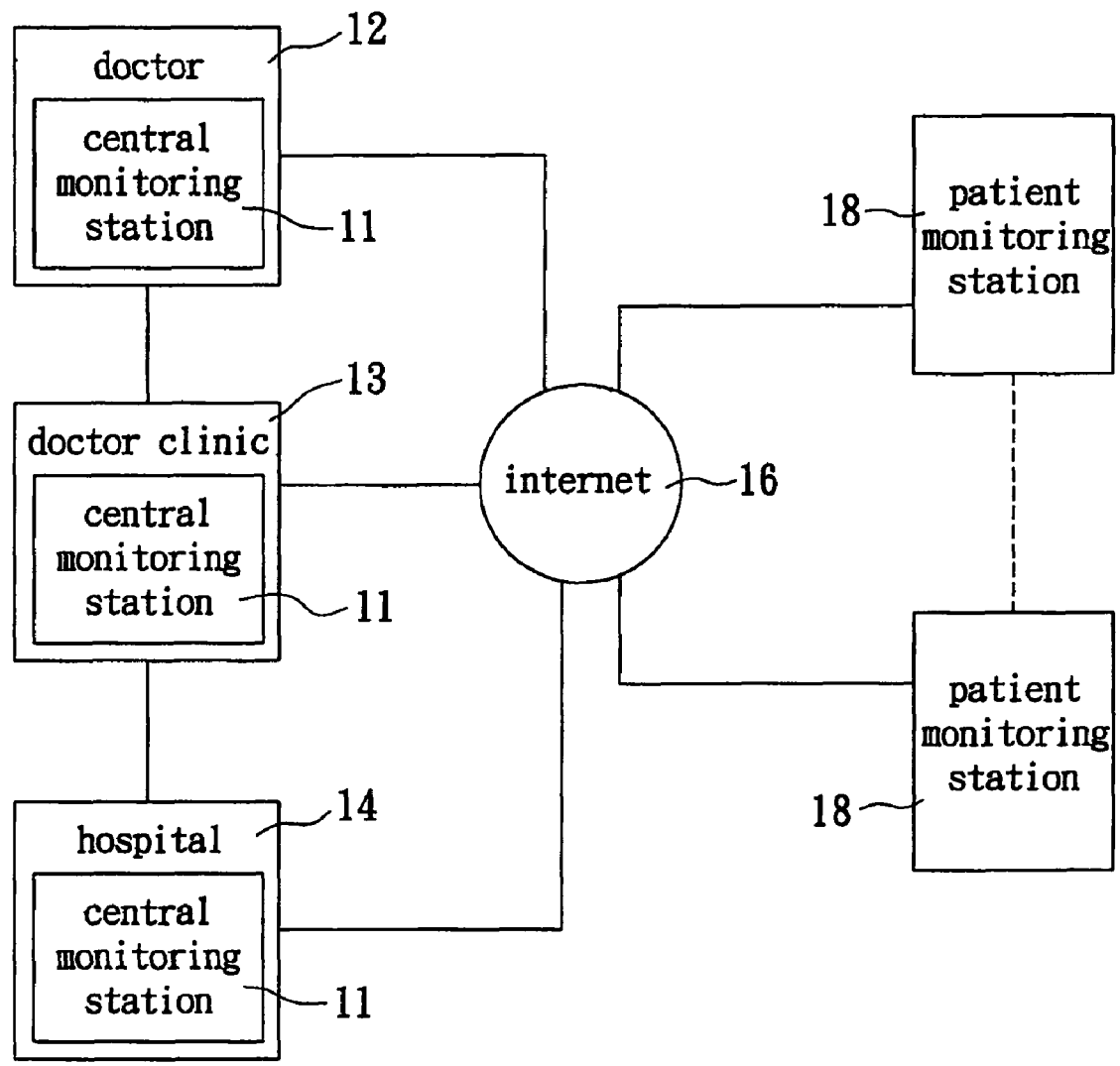
FIG. 1 is a packet-based tele-medicine system diagram of the prior art.
Figure 2:
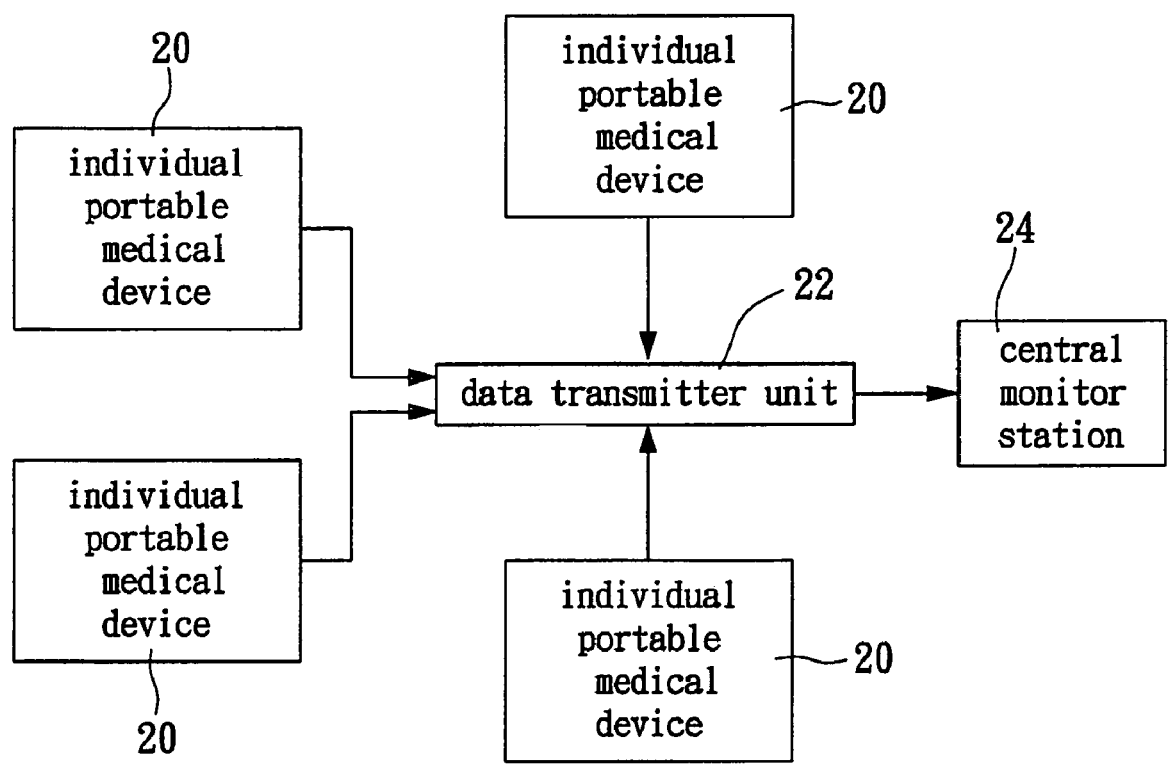
FIG. 2 is a remote home care system diagram of the prior art.
Figure 3:
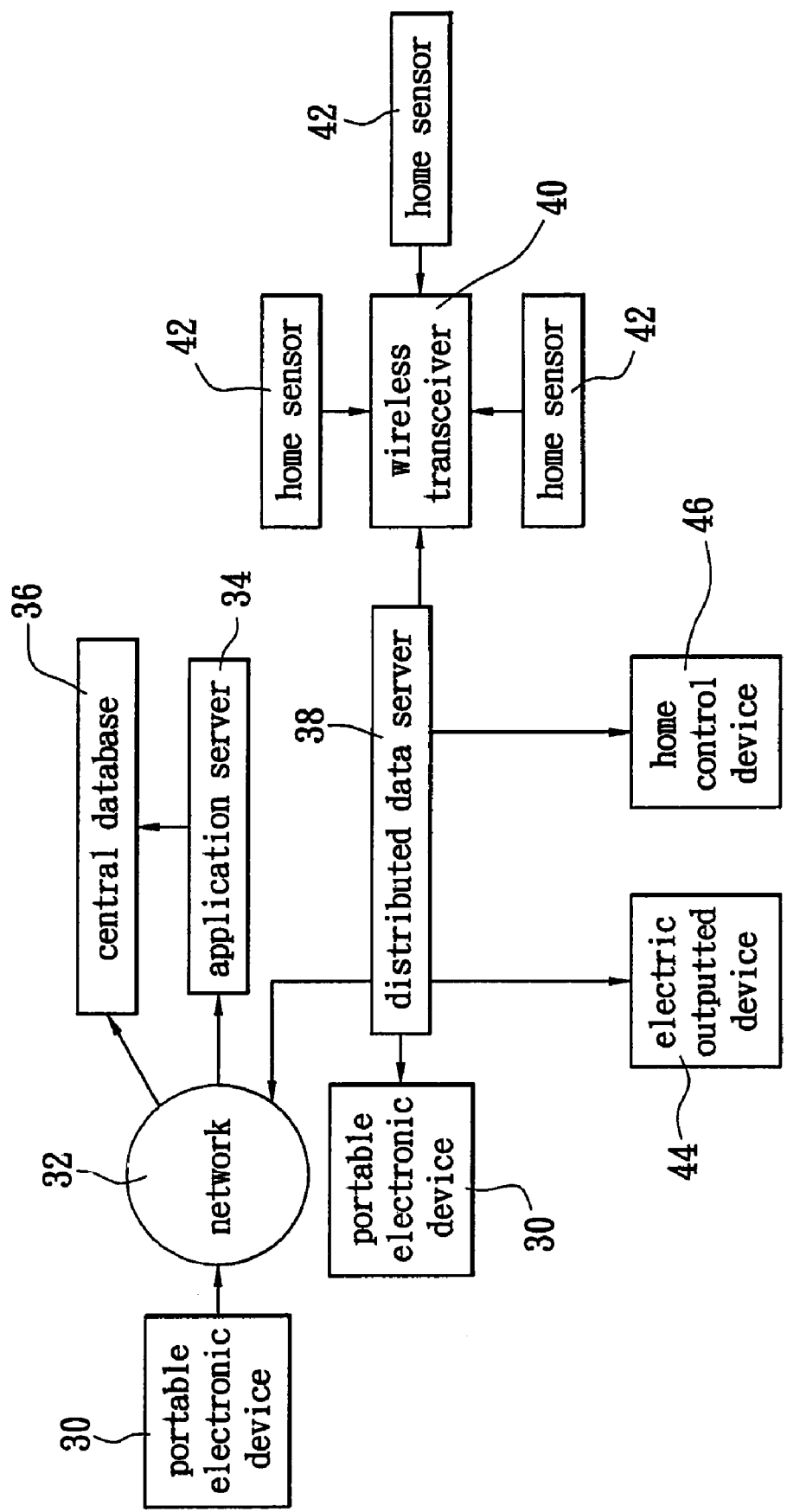
FIG. 3 is a system diagram of the present invention.

Referring to FIG. 3 a system diagram of the present invention is shown. The system includes a distributed data server 38 connected with a plurality of home sensors 42 via a wireless transceiver 40 using a cable or a wireless manner. The distributed data server 38 receives home monitoring data from the home sensors 42 and processes, analyzes and transmits it. The home sensors 42 are comprised of at least one health sensor and at least one environment sensor. The health sensors are comprised of a body temperature sensor, a pulse sensor, a behavior sensor, and a blood sensor. The environment sensors are comprised of a room temperature sensor, a light sensor, a door/windows sensor, and a warning sensor. The distributed data server 38 transmits the processed home monitoring data to a central database 36 to store via a wireless manner.

When the home sensors 42 detect an irregular signal, the home sensors 42 transmit the irregular signal via the wireless transceiver 40 to the distributed data server 38 for initial processing and judging. Then, the judging result of the distributed data server 38 is transmitted to an electric outputted device 44 or a home control device 46. The electric outputted device 44 may be a mobile phone, a PDA, a notebook, or an e-mail receiver. The judging result of the distributed data server 38 can transmit a message to a mobile phone or an e-mail receiver. The home control device 46 can control the environment for an adjustable environment in accordance with the judging result, for example to cool air, turn on lights or turn on warning equipment.

The distributed data server 38 stores a plurality of user authentication data. Any person can potentially catch the home monitoring data of the distributed data server 38 via a network 32. The person is required to perform a legal authentication process into the distributed data server 38. The legal authentication process may be a password, an account number, identification data, a public or private key and/or a mixture of the above. A user can read or analyze the home monitoring data stored on the distributed data server via Microsoft Internet Explorer or another similar application, such as Netscape or Firefox, on the portable electronic device 30. The customization VB application program or explorer can show the real-time monitoring data of the home sensors 42 except for the home monitoring data stored on the distributed data server 38.

Figure 4:
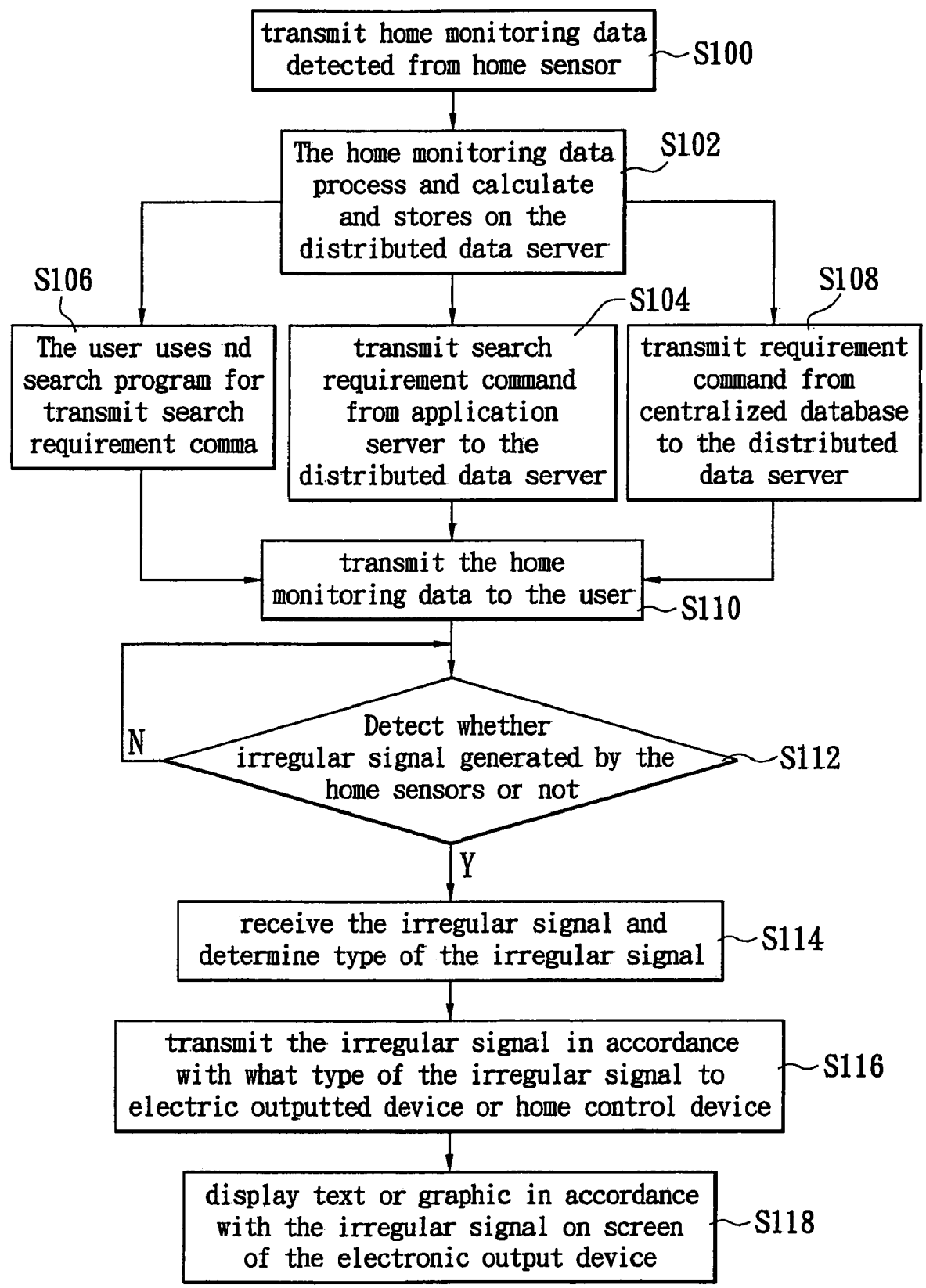
FIG. 4 is a flow chart of an operating method of the present invention.

FIG. 4 is a flow chart of an operating method for the present invention. The method comprises transmitting a plurality of home monitoring data detected from a plurality of home sensors 42 to a distributed data server 38(S100). The home sensors 42 are comprised of at least one health sensor and at least one environment sensor. The health sensors are comprised of a body temperature sensor, a pulse sensor, a behavior sensor, and a blood sensor. The home monitoring data of the distributed data server 38 includes a plurality of user's health data and a plurality of home environment data. The user's health data may include body temperature, blood composition, or pulse and the environmental data may include room temperature, light intensity, or an electronic access device.

The home monitoring data of the home sensors 42 is processed and calculated by the distributed data server 38 and stored in the home monitoring data on the distributed data server 38(S102). A user having passed the authentication process catches the home monitoring data of the distributed data server 38 for using the portable electronic device 30 over a network 32. The user uses a search program for transmitting a search requirement command to the distributed data server via the portable electronic device 30(S106), or transmitting a search requirement command from an application server to the distributed data server (S104), or transmitting a requirement command from a centralized database to the distributed data server in accordance with a fixed time or a batch (S108). The search program may be Microsoft Internet Explorer or any other similar web program combined with an application program. The application program is written using VB or any other programming language. An application server 34 stores the application program of the data and processes, and analyzes the data via the present invention, as well as managing the distributed data server 38, the system program and automatically refreshes the application program.

The distributed data server 38 transmits the home monitoring data to the user (S110). The user can read and analyze the home monitoring data stored on the distributed data server 38 through the application server 34 via Microsoft Internet Explorer or another similar application, such as Netscape or Firefox, on the portable electronic device 30. The customization VB application program or explorer can show the real-time monitoring data of the home sensors 42 except for the home monitoring data stored on the distributed data server 38. The central database 36 catches home monitoring data from the distributed data server 38 for either a fixed time or in a batch manner.

To detect whether an irregular signal has been generated by the home sensors or not (S112) the distributed data server 38 has an event driven transmitting message function. When the home sensors 42 emit an irregular signal, the distributed data server 38 receives the irregular signal and determines what type of irregular signal (S114) it is. If the detection result is no, then the process returns to S112. The distributed data server 38 transmits the irregular signal in accordance with what type of irregular signal the signal is transmitted to an electric outputted device 44 or a home control device 46 (S116). To display text or graphics in accordance with the irregular signal on a screen of the electronic output device (S118) the type of irregular signal depends upon the user's health alarm or the home environment alarm. The electronic output device is a mobile phone or an e-mail receiving device. The distributed data server 38 transmits an E-mail or a mobile phone message to a special E-mail address or a mobile phone number, or the distributed data server 38 judges the environment sensor signal to drive the turn on/turn off function of an air cooler, a door, a light or an alarm.

The system of the present invention is used for environmental monitoring or health monitoring. The user or manager can catch monitor data from the distributed data server 38 and use a VB application program or web program via TCP/IP and HTTP protocol. The kernel of a system is a micro-controller combined with a network chipset. The system of the present invention can connect with a distributed data server in the network, so that the system has a small size, a low cost and high data security.

However, in the description mentioned above, only the preferred embodiments according to this invention are provided without limit to claims of this invention; all those skilled in the art without exception should include the equivalent changes and modifications as falling within the true scope and spirit of the present invention.

What is claimed is:

1. A portable tele-homecare monitoring system, comprising:
   a distributed data server;
   a centralized database coupled to the distributed data server for storing a plurality of health data and home environment of a plurality of users;
   an application server coupled to the distributed data server and the centralized database and having an application program;
   a plurality of home sensors coupled to the distributed data server for detecting the health data and the environmental data of the users; and
   a portable electronic device embedded with a browser for coupling to the application server through a network, accessing the health data and the environmental data of the users via the application program and for remotely reviewing the health data and the environmental data displayed on the browser.

2. The system according to claim 1, further comprising a wireless transceiver for coupling to the distributed data server.

3. The system according to claim 1, further comprising at least one home control device for coupling to the distributed data server.

4. The system according to claim 1, further comprising at least one electric outputted device for coupling to the distributed data server.

5. The system according to claim 4, wherein the electric outputted devices is a mobile phone, a PDA, a notebook or an e-mail receiver.

6. The system according to claim 1, wherein the home sensor includes a plurality of health sensors and a plurality of environment sensors.

7. The system according to claim 6, wherein the environment sensors include a body temperature sensor, a pulse sensor, a behavior sensor, and a blood sensor.

8. The system according to claim 6, wherein the environment sensor includes a room temperature sensor, a light sensor, a door/window sensor, and a warning sensor.

9. A method of facilitating portable tele-homecare monitoring through a portable tele-homecare monitoring system having a distributed data server, a centralized database coupled to the distributed data server, an application server coupled to the distributed data server and the centralized database, a plurality of home sensors coupled to the distributed data server, and a portable electronic device embedded with a browser, comprising:

transmitting a plurality of home monitoring data detected from a by the home sensors to the distributed data server;

storing, processing and calculating the home monitoring data transmitted from the home sensors by the distributed data server;

receiving a search requirement command transmitted through a network from the portable electronic device by the distributed data server wherein upon a receipt of the search requirement command the distributed data server executes a corresponding search program; and transmitting the home monitoring data required by the search program to the portable electronic device from the distributed data server.

10. The method according to claim 9, wherein the home monitoring data includes a plurality of the user's health data and a plurality of environmental data.

11. The method according to claim 10, wherein the user's health data is a body temperature, a blood composition, or a pulse.

12. The method according to claim 10, wherein the environmental data comprises a room temperature, a light intensity, or an electronic access device.

13. The method according to claim 9, wherein the search program is a browser program combined with an application program.

14. The method according to claim 9, after storing, processing and calculating the home monitoring data further comprising:

receiving the search requirement command from a centralized database periodically or in a batch from an application server by the distributed data server.

15. The method according to claim 13, wherein the application program is written using a programming language.

16. The method according to claim 9, further comprising:

detecting whether an irregular signal has been generated by the home sensors or not;

receiving the irregular signal and determining a type of the irregular signal transmitted by the distributed data server when detecting the irregular signal has been generated by the home sensors; and transmitting the irregular signal in accordance with the type of the irregular signal determined by the distributed data server to an electric output device or a home control device.

17. The method according to claim 16, further comprising displaying text or graphics in accordance with the irregular signal on a screen of the electronic output device.

18. The method according to claim 16, further comprising repeatedly detecting whether a irregular signal has been generated by the home sensors or not when no irregular signal generated by the home sensors has been detected.

19. The method according to claim 16, wherein the type of irregular signal include the user's health alarm or the home environment alarm.

20. The method according to claim 16, wherein the electronic output device is a mobile phone or an e-mail receiving device.

\* \* \* \* \*